(12) United States Patent  
Fukuda

(10) Patent No.: US 7,727,769 B2  
(45) Date of Patent: Jun. 1, 2010

(54) MEASUREMENT RESULT CORRECTION METHOD, URINE ANALYSIS SYSTEM, AND URINE ANALYZER

(75) Inventor: Masakazu Fukuda, Kobe (JP)

(73) Assignee: Sysmex Corporation, Hyogo (JP)

( * ) Notice: Subject to any disclaimer, the term of this patent is extended or adjusted under 35 U.S.C. 154(b) by 815 days.

(21) Appl. No.: 11/236,729

(22) Filed: Sep. 28, 2005

(65) Prior Publication Data

US 2006/0073606 A1 Apr. 6, 2006

(30) Foreign Application Priority Data

Sep. 29, 2004 (JP) ............................ 2004-285259

(51) Int. Cl.
*G01N 31/00* (2006.01)
*G01N 27/00* (2006.01)
*G01N 21/00* (2006.01)
*C12Q 1/54* (2006.01)

(52) U.S. Cl. ............................ 436/149; 436/8; 436/10; 436/14; 436/15; 436/16; 356/73; 422/50

(58) Field of Classification Search ............... 436/8–19, 436/149; 702/19; 356/73; 422/63

See application file for complete search history.

(56) References Cited

U.S. PATENT DOCUMENTS

| 5,325,168 | A | | 6/1994 | Nakamoto et al. |
| 5,757,475 | A | * | 5/1998 | Katayama et al. ............. 356/73 |
| 6,021,339 | A | * | 2/2000 | Saito et al. .................. 600/345 |
| 6,183,697 | B1 | * | 2/2001 | Tanaka et al. ............ 422/82.05 |
| 6,306,660 | B1 | | 10/2001 | Messenger et al. |
| 2007/0072301 | A1 | * | 3/2007 | Fukuda et al. ................ 436/50 |

FOREIGN PATENT DOCUMENTS

| JP | 2-27262 A | 1/1990 |
| JP | 11-118796 | 4/1999 |
| JP | 2001-153871 | 6/2001 |

* cited by examiner

*Primary Examiner*—Jill Warden
*Assistant Examiner*—Dean Kwak
(74) *Attorney, Agent, or Firm*—Sughrue Mion, PLLC

(57) ABSTRACT

A urine analysis system includes a urinary particle analyzer and a computer. The urinary particle analyzer has a measuring unit that measures a cast concentration from the urine and an electric conductivity sensor that measures the electric conductivity of the urine. The computer has a function of correcting the cast concentration measured by the measuring unit on the basis of the electric conductivity of the urine measured by the electric conductivity sensor and a function of outputting the corrected cast concentration.

16 Claims, 14 Drawing Sheets

FIG.14

Protein: +2,+3   Number of specimens: 52

|  | Without correction | With correction |
|---|---|---|
| Cast positive flag | 12 | 17 |

Protein: +1   Number of specimens: 22

|  | Without correction | With correction |
|---|---|---|
| Cast positive flag | 2 | 4 |

Protein: ±   Number of specimens: 10

|  | Without correction | With correction |
|---|---|---|
| Cast positive flag | 1 | 2 |

Protein: 0   Number of specimens: 144

|  | Without correction | With correction |
|---|---|---|
| Cast positive flag | 5 | 6 |

MEASUREMENT RESULT CORRECTION METHOD, URINE ANALYSIS SYSTEM, AND URINE ANALYZER

FIELD OF THE INVENTION

The present invention relates to a measurement result correction method for correcting a measurement result in urine analysis, a urine analysis system and a urine analyzer used in carrying out the method, and a computer readable storage medium that stores a computer program for making a computer correct a measurement result.

BACKGROUND OF THE INVENTION

As a urine analyzer used in urine tests, a urine qualitative analyzer and a urinary particle analyzer are widely known. A urine qualitative analyzer is generally constructed in such a manner that a test paper having a reaction test piece stuck thereon for each measurement item is immersed in an analyte urine sample for a predetermined period of time, and the color of the test piece is compared with standard colors for determination so as to obtain the results of negative/positive (−), (±), (+), . . . automatically for each item (See, for example, Japanese Laid-open Patent Publication No. 2-27262). Also, a urinary particle analyzer is constructed to classify and count the particles in an analyte urine sample automatically (See, for example, U.S. Pat. No. 5,325,168).

One of the measurement items of the urine qualitative analyzer such as described above is protein concentration. Since protein is reabsorbed by renal tubes in the normal kidney, this protein concentration is used as an index that indicates the reabsorption capability of the kidney. However, depending on the condition of a patient (person to be tested), the urine is sometimes concentrated or diluted, so that it may not be possible to grasp the amount of excreted protein in urine correctly by random urine. By a current protein test paper, with a diluted urine, a clinically significant proteinuria (namely, a specimen that should be evaluated as being positive) may be evaluated as being negative or conversely, with concentrated urine, those that should be evaluated as being negative may be evaluated as being positive.

In view of the above, a method is proposed in which a creatinine concentration in an analyte urine sample is measured by the colorimetry so as to correct the result of measurement of the concentration of albumin, which is one kind of protein, with the creatinine concentration (See U.S. Pat. No. 6,306,660). Since this creatinine concentration reflects the degree of concentration of the urine, such correction can remove the influence of concentration or dilution of the urine from the result of measurement of albumin concentration.

However, with the above-described method of correction of the protein concentration disclosed in U.S. Pat. No. 6,306,660, the creatinine concentration is measured by the colorimetry; however, the creatinine concentration measurement using the colorimetry such as described above has a low resolution due to its structure, thereby raising a problem of low correction precision.

SUMMARY OF THE INVENTION

The scope of the present invention is defined solely by the appended claims, and is not affected to any degree by the statements within this summary.

The present invention has been made in view of the above circumstances, and an object thereof is to provide a measurement result correction method having a higher correction precision than in the prior art and being capable of obtaining a highly reliable measurement result in urine analysis, a urine analysis system and a urine analyzer used in carrying out the method, and a computer readable storage medium that stores a computer program for making a computer correct a measurement result.

The first aspect of the present invention relates to a measurement result correction method comprising the steps of measuring a concentration of a component that is related to a kidney condition from urine, measuring an electric conductivity of said urine, and correcting the measured concentration of the component on a basis of the measured electric conductivity of the urine.

The second aspect of the present invention relates to a measurement result correction system comprising a first measuring unit that measures a concentration of a component that is related to a kidney condition from urine, a second measuring unit that measures an electric conductivity of said urine, a correction means that corrects the concentration of the component measured by said first measuring unit on a basis of said electric conductivity of the urine measured by said second measuring unit, and an output means that outputs the corrected concentration of the component obtained by said correction means.

The third aspect of the present invention relates to a urine analyzer comprising a first measuring unit that measures a concentration of a component that is related to a kidney condition from urine, a second measuring unit that measures an electric conductivity of the urine, a correction means that corrects the concentration of the component measured by said first measuring unit on a basis of said electric conductivity of the urine measured by said second measuring unit, and an output means that outputs the corrected concentration of the component obtained by said correction means.

The fourth aspect of the present invention relates to a computer readable storage medium that stores a computer program for making a computer correct a measurement result of urine, wherein said computer program comprises a first obtaining means for making said computer obtain a concentration of a component that is contained in urine and related to a kidney condition, a second obtaining means for making said computer obtain an electric conductivity of the urine, a correction means for making said computer correct the concentration of the component obtained by said first obtaining means on a basis of the electric conductivity of the urine obtained by said second obtaining means, and an output means for making said computer output the corrected concentration of the component obtained by said correction means.

BRIEF DESCRIPTION OF THE DRAWINGS

FIG. 14 is a view table showing a result of an experiment in which the result of measurement of cast concentration without correction and the corrected result of measurement of cast concentration are compared.

DETAILED DESCRIPTION OF THE EMBODIMENT

Hereafter, an embodiment of the present invention will be described with reference to the attached drawings.

Figure 1:
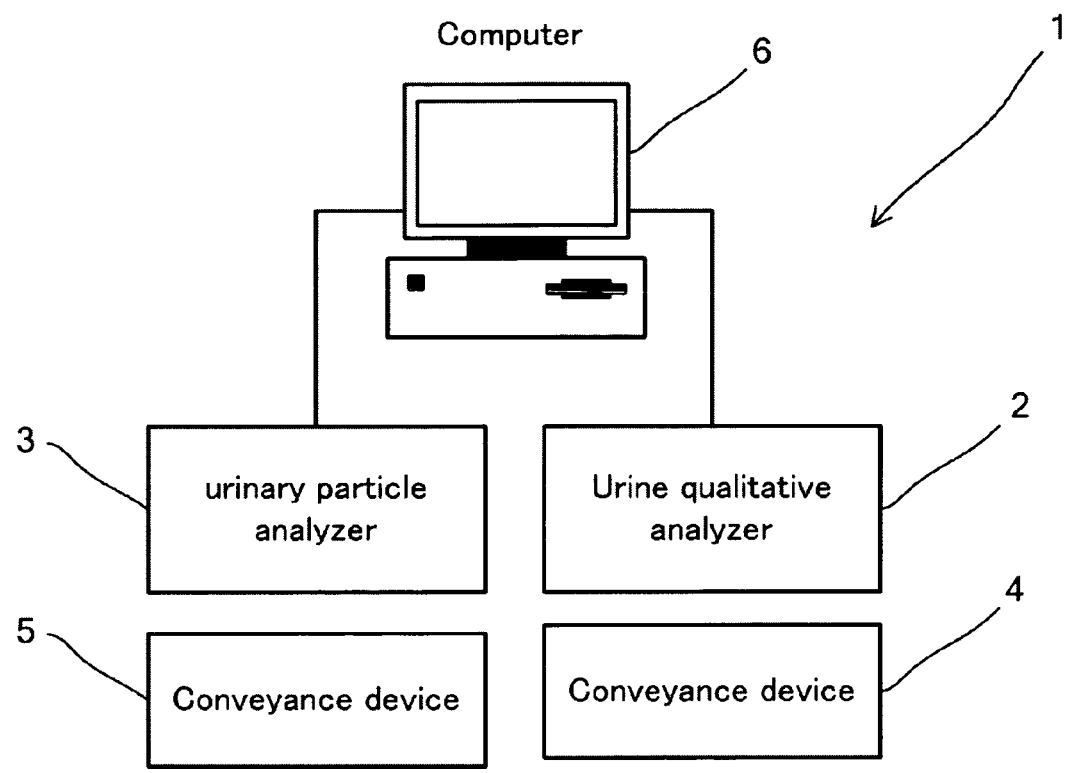
FIG. 1 is a model view illustrating a construction of a urine analysis system according to an embodiment of the present invention.

FIG. 1 is a model view illustrating a construction of a urine analysis system according to an embodiment of the present invention. As described in FIG. 1, a urine analysis system 1 according to this embodiment is mainly constructed with a urine qualitative analyzer 2, a urinary particle analyzer 3, conveyance device 4 and 5, and a computer 6. The computer 6 is electrically connected to the urine qualitative analyzer 2 and the urinary particle analyzer 3, thereby being capable of mutual data communication with the urine qualitative analyzer 2 and the urinary particle analyzer 3.

Figure 2:
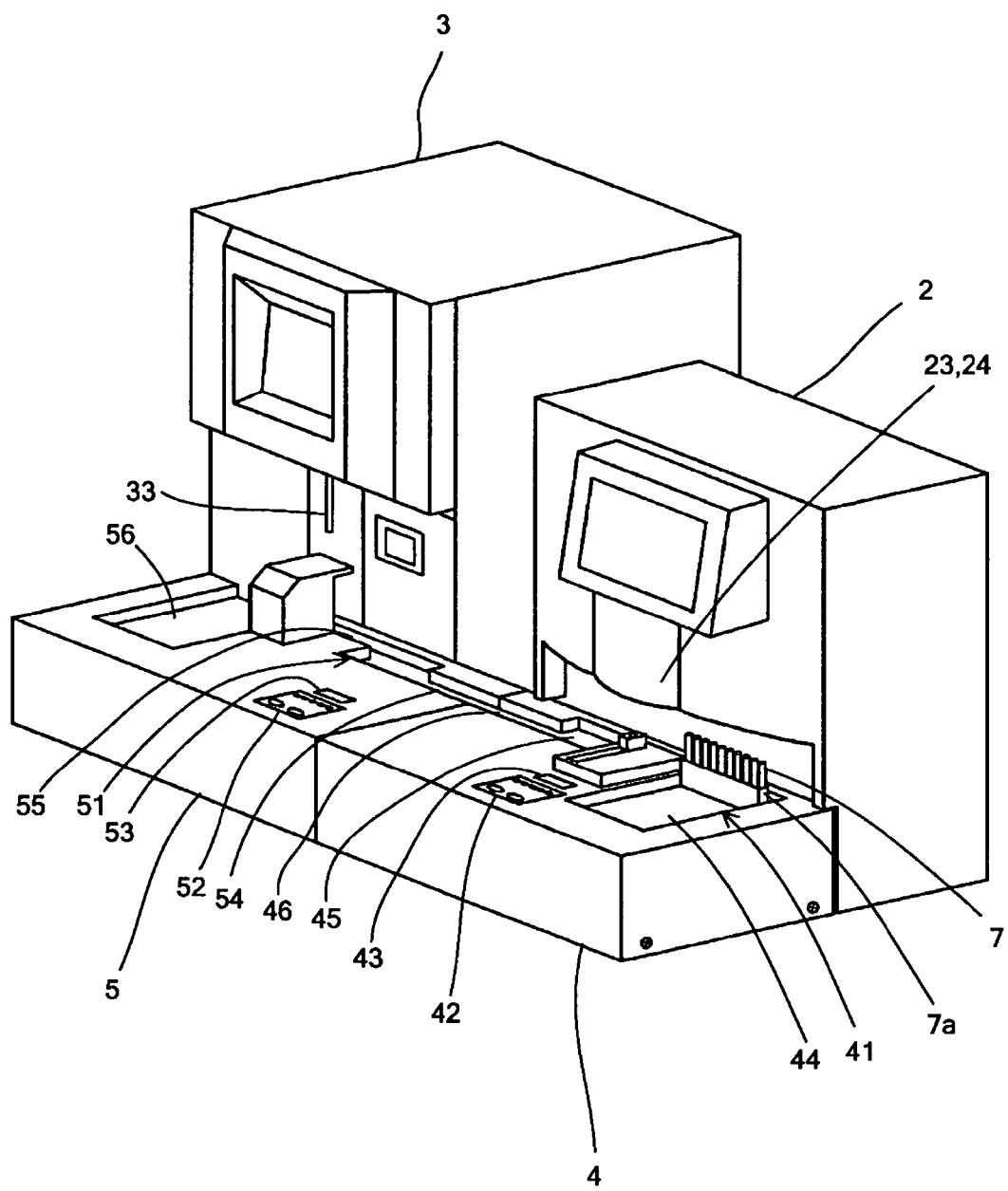
FIG. 2 is a perspective view illustrating a partial construction of a urine analysis system according to an embodiment of the present invention.

FIG. 2 is a perspective view illustrating a partial construction of the urine analysis system 1 according to this embodiment. Referring to FIG. 2, the urine qualitative analyzer 2 and the urinary particle analyzer 3 are arranged to be adjacent to each other, and the conveyance device 4 is disposed in front of the urine qualitative analyzer 2 and the conveyance device 5 is disposed in front of the urinary particle analyzer 3. The conveyance device 4 and the conveyance device 5 are joined with each other with a bolt or the like, so as to be capable of continuously transporting a specimen between the conveyance device 4 and the conveyance device 5, as will be described later. The conveyance device 4 is constructed to be capable of automatically supplying a specimen to the urine qualitative analyzer 2, and the conveyance device 5 is constructed to be capable of automatically supplying the specimen received from the conveyance device 4 to the urinary particle analyzer 3.

Figure 3:
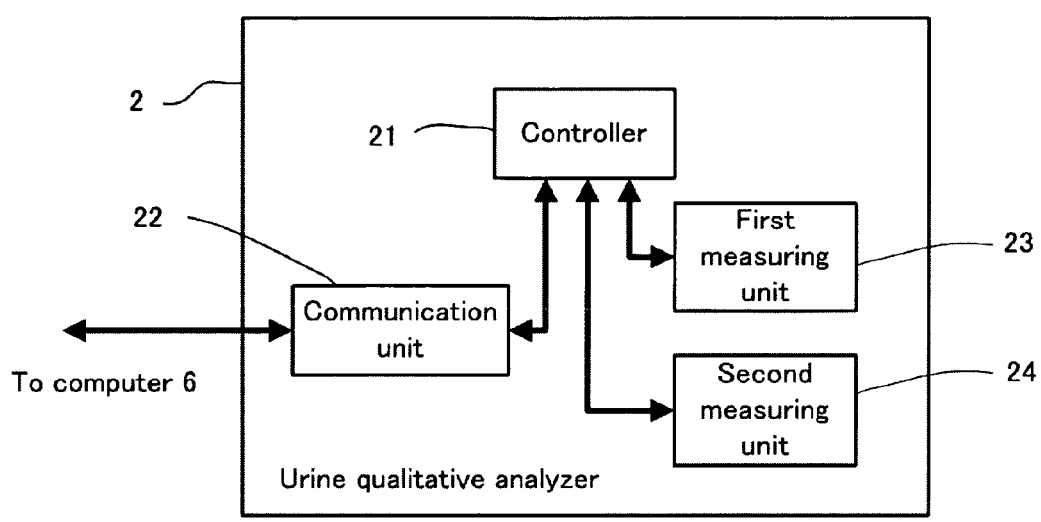
FIG. 3 is a block diagram showing a construction of a urine qualitative analyzer.

FIG. 3 is a block diagram showing a construction of the urine qualitative analyzer 2. Referring to FIG. 3, the urine qualitative analyzer 2 is mainly constructed with a controller 21 including a CPU, a ROM, a RAM, and the like, a communication unit 22 that transmits and receives data to and from the computer 6, a first measuring unit 23 that immerses a test paper corresponding to each measurement item (occult blood concentration, protein concentration, white blood cell concentration (white blood cell esterase reaction), nitrite concentration, and glucose concentration) into a supplied specimen and makes measurements on each measurement item from the degree of change in the color of each test paper, and a second measuring unit 24 that detects the refractive index of the specimen and measures the specific gravity of the specimen in accordance with the refractive index. The urine qualitative analyzer 2 such as described above is constructed to be capable of automatically classifying the degree of change in the color of the test paper into nine stages of (−), (±), (+), (2+), (3+), . . . , (7+) and transmitting the measurement result data corresponding to each from the communication unit 22 to the computer 6 in the cases of occult blood concentration, protein concentration, white blood cell concentration, nitrite concentration, and glucose concentration, and transmitting the measurement result data showing the measured value of the specific gravity from the communication unit 22 to the computer 6.

Figure 4:
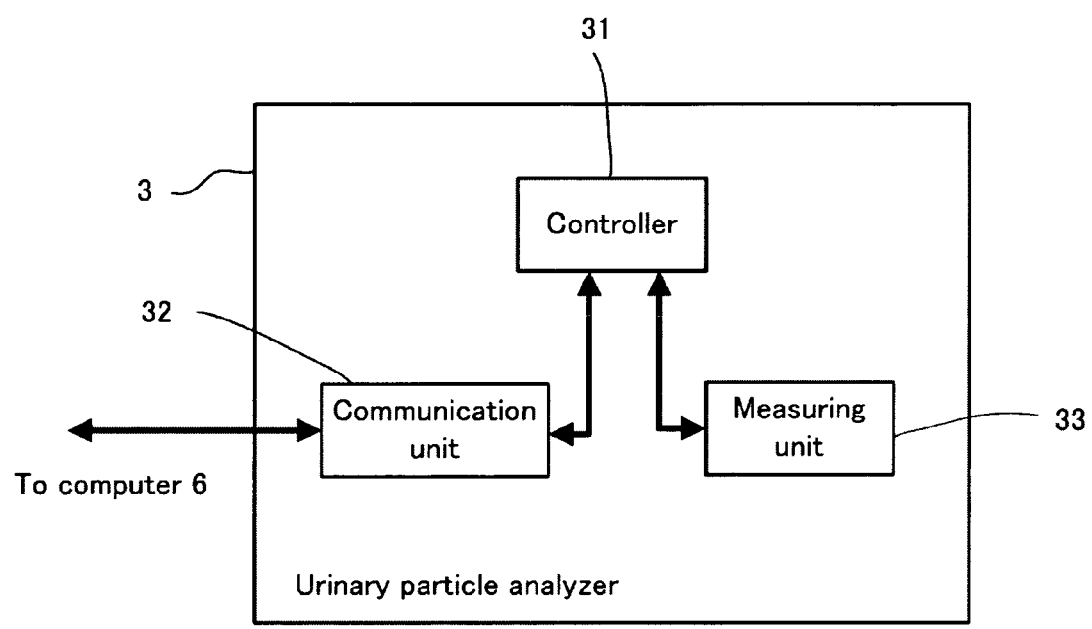
FIG. 4 is a block diagram showing a construction of a urinary particle analyzer.

FIG. 4 is a block diagram showing a construction of the urinary particle analyzer 3. Referring to FIG. 4, the urinary particle analyzer 3 is mainly constructed with a controller 31 including a CPU, a ROM, a RAM, and the like, a communication unit 32 that transmits and receives data to and from the computer 6, and a measuring unit 33 for obtaining a measured value of each measurement item on the urinary particles (red blood cells, white blood cells, casts, bacteria, and the like) by the flow cytometry method on a supplied specimen.

Figure 5:
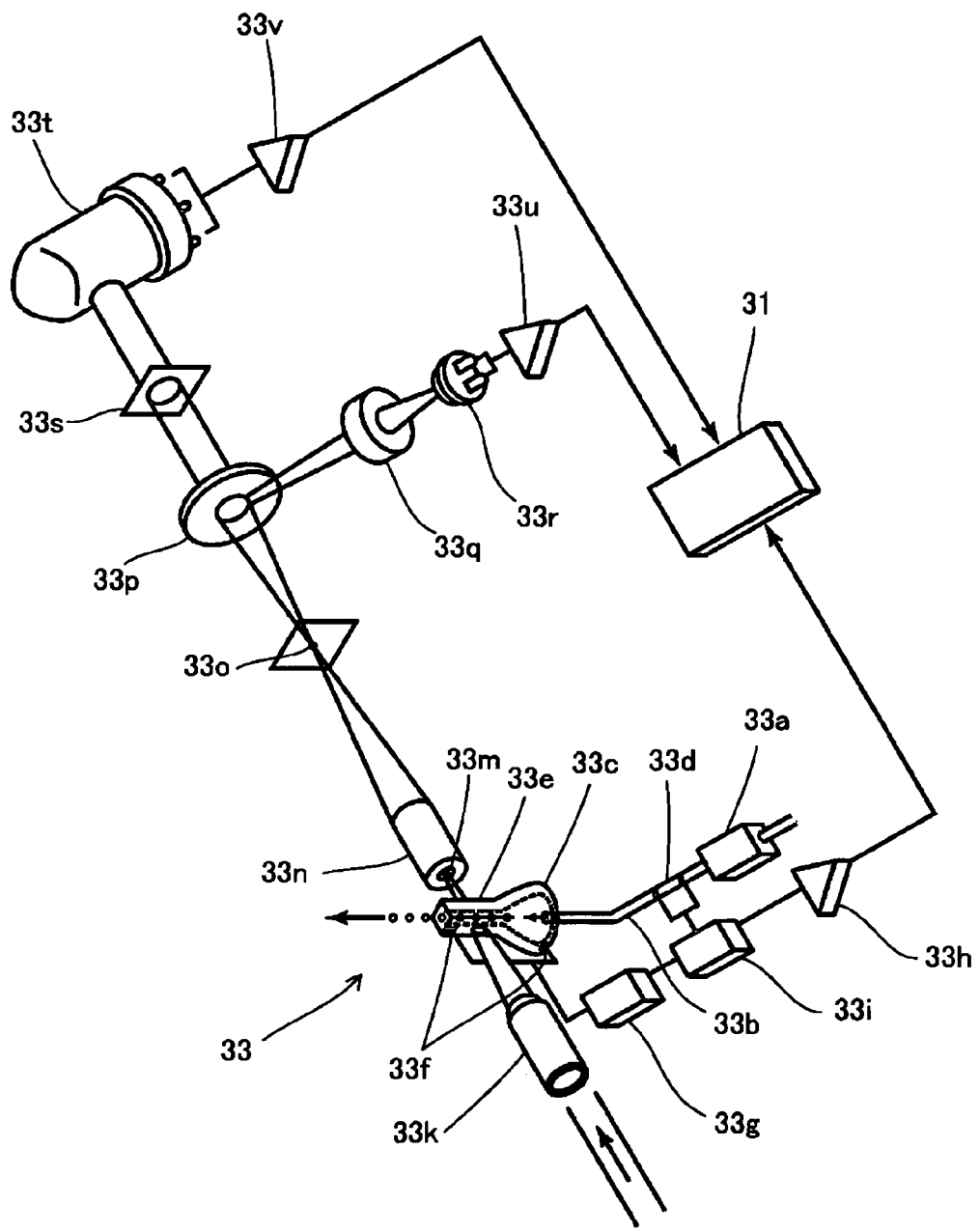
FIG. 5 is a model view illustrating a construction of an essential part of the urinary particle analyzer.

FIG. 5 is a model view illustrating a construction of an essential part of the urinary particle analyzer 3. The measuring unit 33 has a reaction unit 33a, and sucks a urine specimen (sample) transported by the conveyance device 5 with a sample suction pipette (not illustrated) and introduces the sample together with a diluted solution and a stain solution to the reaction unit 33a. In the reaction unit 33a, the sample is mixed with the diluted solution and the stain solution, whereby the urine is diluted by four times. The reaction unit 33a has an agitator and a temperature controller having a heater such as a thermistor, thereby agitating the introduced sample and at the same time performing temperature control to stain the sample for 10 seconds at a constant temperature of 35° C.

A flow passageway 33b is disposed to extend from the reaction unit 33a, and a sheath flow cell 33c is disposed at an end of the flow passageway 33b. Also, to the middle of this flow passageway 33b, an electric conductivity sensor 33d is mounted. The sample diluted and stained in the reaction unit 33a is sent to the sheath flow cell 33c via the flow passageway 33b. Also, a sheath liquid chamber (not illustrated) is disposed in the measuring unit 33, and a sheath liquid pooled in this sheath liquid chamber is supplied to the sheath flow cell 33c. In the sheath flow cell 33c, the sample flows so as to be surrounded by the sheath liquid. An orifice 33e is disposed in the sheath flow cell 33c, and the flow of the sample is narrowed by this orifice 33e, whereby the particles (tangible components) contained in the sample pass through the orifice 33e one by one. In the sheath flow cell 33c, a pair of electrodes 33f is attached to sandwich the orifice 33e. A direct current power source 33g is connected to these electrodes 33f, whereby a direct current is supplied between the electrodes 33f. While the direct current is being supplied from the direct current power source 33g, an impedance between the electrodes 33f is detected. In this way, an electric resistance signal indicating a change in the impedance is amplified by an amplifier 33h and given to the controller 31. This electric resistance signal reflects the volume information of each particle, so that the controller 31 performs signal processing on this electric resistance signal to obtain the volume of the particle.

Figure 6:
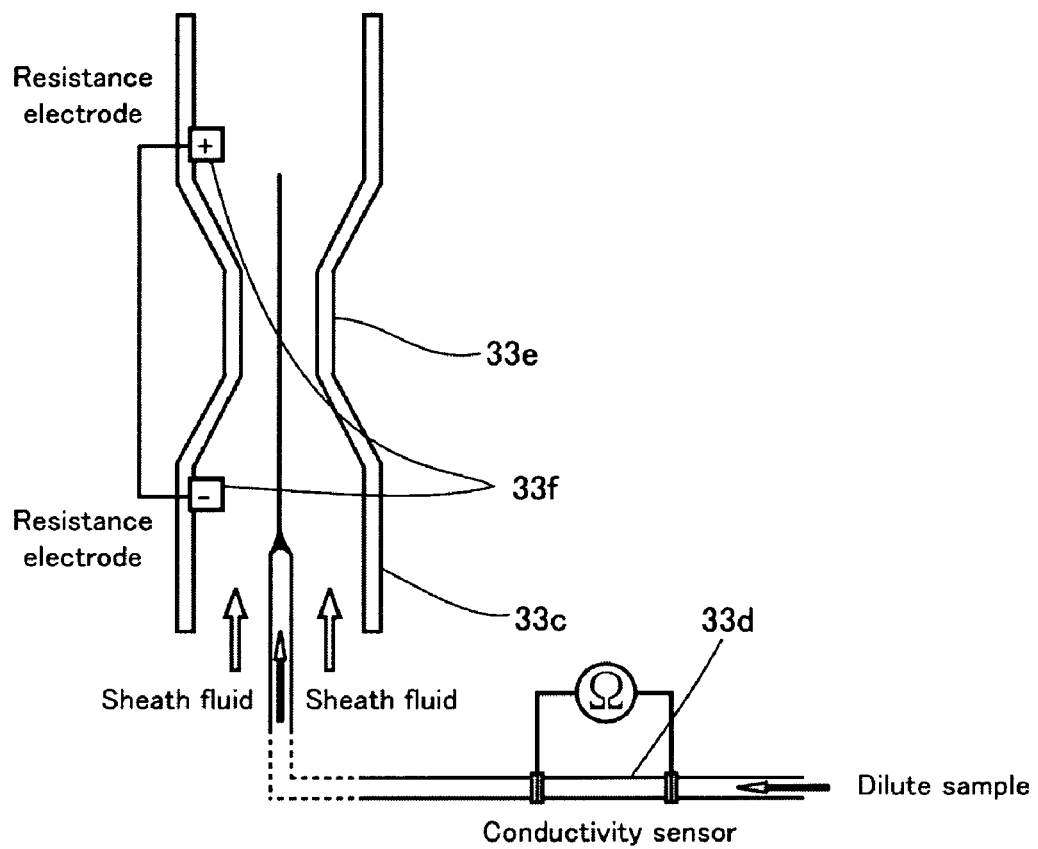
FIG. 6 is a model view illustrating a construction of a sheath flow cell and its neighborhood for describing sensitivity adjustment in impedance measurement by electric conductivity.
Figure 7:
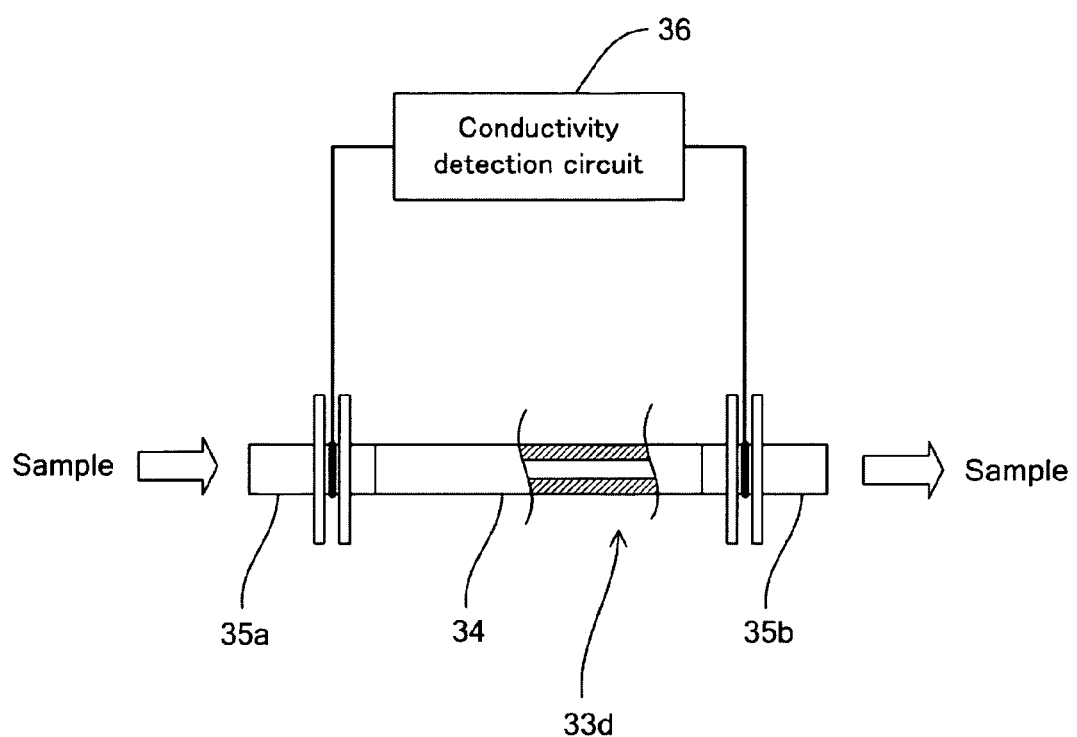
FIG. 7 is a partial cross-sectional side view illustrating a construction of an electric conductivity sensor according to an embodiment of the present invention.

Also, before being supplied to the sheath flow cell 33c, the sample passes through the flow passageway 33b, where the electric conductivity is detected by the electric conductivity sensor 33d. The electric conductivity detected by the electric conductivity sensor 33d is given to an electric current control circuit 33i, and the electric current control circuit 33i controls the output current of the direct current power source 33g in accordance with this electric conductivity. FIG. 6 is a model view illustrating a construction of the sheath flow cell 33c and its neighborhood for describing sensitivity adjustment in impedance measurement by electric conductivity, and FIG. 7 is a partial cross-sectional side view illustrating a construction of the electric conductivity sensor 33d. The electric conductivity of a urine sample varies sample by sample. When the electric conductivity of the sample changes, the electric current between the electrodes 33f changes irrespective of the presence or absence of passage of a particle. This affects the sensitivity of impedance measurement, making it impossible to obtain correct volume information on the particle. Therefore, in the measuring unit 33, the electric conductivity of the sample is controlled to be within a constant range by dilution with a urinopack (diluted solution). Also, the electric conductivity is measured before the diluted sample enters the sheath flow cell 33c and, in accordance with the measured value, the detected electric current is corrected to adjust the sensitivity to be constant. Here, the structure of the electric conductivity sensor 33d will be described with reference to FIG. 7. The electric conductivity sensor 33d as a whole has a nearly tube-like shape, and is mainly constructed with an insulation tube 34 made of an insulator such as synthetic resin or ceramics and metal electrodes 35a, 35b mounted to the two ends of the insulation tube 34. The metal electrodes 35a, 35b have an annular shape having the same inner diameter as the insulation tube 34, and are coaxially mounted to the insulation tube 34. By this, a cavity having the same inner diameter is formed in the electric conductivity sensor 33d along its entire length. An electric conductivity detecting circuit 36 is connected to the metal electrodes 35a, 35b. When a sample passes through the cavity, a sinusoidal current of about 1 kHz is given between the metal electrodes 35a, 35b, and the electric current that flows in the sample passing through the cavity is rectified and integrated by the electric conductivity detecting circuit 36, so as to obtain a voltage proportional to the electric conductivity of this sample. A voltage signal (analog signal) indicating this electric conductivity is converted into a digital signal by an A/D converter (not illustrated). In many cases, such A/D conversion is realized by an A/D converter having a resolution of 8 to 16 bits, thereby ensuring a resolution of such a degree that the protein concentration and the cast concentration described later can be corrected at a sufficiently high precision. The electric conductivity signal obtained in this manner is then output to the electric current control circuit 33i.

Further, the electric current control circuit 33i is adapted to output the input electric conductivity signal to the controller 31. Also, when the sample changes in temperature, the electric conductivity changes in accordance with the temperature change because an ionized substance is different. However, since the samples are controlled to have a constant temperature as described above, the electric conductivity can be measured under the same condition, whereby a highly precise measurement result of electric conductivity can be obtained.

In the measuring unit 33, an argon laser light source is disposed to emit a laser beam toward the orifice 33e of the sheath flow cell 33c. A radiation lens system 33k made of plural lenses is disposed between the argon laser light source and the sheath flow cell 33c. By this radiation lens system 33k, parallel beams emitted from the argon laser light source are converged into a beam spot. This beam spot has an elliptical shape, and is focused at the center of the sheath flow cell 33c. Also, on the optical axis of the laser beams from the argon laser light source, a collector lens 33n having a beam stopper 33m is disposed to oppose the radiation lens system 33k with the sheath flow cell 33c sandwiched in between. The direct light from the argon laser light source is stopped by the beam stopper 33m.

When a sample flows through the sheath flow cell 33c, the laser beams generate optical signals of scattered light and fluorescence. Among these, the forward signal light is collected by the collector lens 33n and is sent to a light-receiving system located at a later stage. The light-receiving system has a pinhole 33o, and further has a dichroic filter 33p on the downstream side of the optical axis. After removal of stray light (light other than the light to be measured) with the pinhole 33o, the signal light sent from the collector lens 33n is divided into a scattered light component and a fluorescence component by the dichroic filter 33p. A lens 33q for collecting the scattered light and a photodiode 33r are disposed at the side (in a direction intersecting the aforementioned optical axis) of the dichroic filter 33p. A color glass filter 33s and a photomultiplier tube 33t are disposed on the downstream side of the aforementioned optical axis of the dichroic filter 33p. The scattered light component divided by the dichroic filter 33p is collected by the lens 33q and then subjected to photoelectric conversion by the photodiode 33r. In this way, an electric signal (scattered light signal) generated by this photoelectric conversion is amplified by an amplifier 33u, and is output to the controller 31. This scattered light signal reflects information on the size of the particle. By performing signal processing on this scattered light signal, the controller 31 obtains the cross-sectional area and the length of the particle. Also, after being subjected to wavelength selection by the color glass filter 33s, the fluorescence component emitted from the dichroic filter 33p is subjected to photoelectric conversion by the photomultiplier tube 33t. An electric signal (fluorescence signal) generated by this photoelectric conversion is amplified by an amplifier 33v, and is output to the controller 31. The fluorescent dye used here has a property of staining the nucleus of the particle in a specific manner. By performing signal processing on this fluorescence signal, the controller 31 obtains the stainability and the length of the stained site of the particle.

In this manner, the electric resistance signal, the electric conductivity signal, the scattered light signal, and the fluorescence signal are given from the measuring unit 33 to the controller 31. By performing signal processing on the electric resistance signal, the scattered light signal, and the fluorescence signal, the controller 31 obtains the red blood cell concentration, the white blood cell concentration, the bacteria concentration, the cast concentration, the epithelial cell concentration, and the like of the sample, and transmits these measurement result data from the communication unit 32 to the computer 6. Further, the urinary particle analyzer 3 is constructed to transmit the measurement result data of the electric conductivity, which is obtained by the controller 31, from the communication unit 32 to the computer 6.

Further, the construction of the conveyance device 4, 5 will be described. Referring to FIG. 2, the conveyance device 4 includes a conveyor 41 for transporting a specimen rack 7a that houses a plurality of (for example, 10) specimen containers 7 in which a specimen is housed, an input panel 42 with which the user performs inputs of various setting values to the conveyance device 4, and an LCD panel 43 for displaying set conditions and the like of the conveyance device 4. The conveyor 41 is constructed with a sending unit 44 with which the user sets the specimen rack 7a that houses specimens as objects of analysis, a lateral conveyor 45 for moving the specimen containers 7, which are housed in the specimen rack 7a set in the sending unit 44, to a measurement position for subjecting the specimens to the measurements of the first measuring unit 23 and the second measuring unit 24 of the urine qualitative analyzer 2, and a discharging unit 46 for moving the specimen rack 7a that has gone through the measurement by the urine qualitative analyzer 2 to the conveyance device 5. The conveyance device 5 includes a conveyor 51 for transporting a specimen rack 7a that houses a plurality of specimen containers 7 in which a specimen is housed, an input panel 52 with which the user performs inputs of various setting values to the conveyance device 5, and an LCD panel 53 for displaying set conditions and the like of the conveyance device 5. The conveyor 51 is constructed with a sending unit 54 that receives the specimen rack 7a from the conveyance device 4, a lateral conveyor 55 for moving the specimen containers 7, which are housed in the received specimen rack 7a, to a measurement position for subjecting the specimens to the measurement of the measuring unit 33 of the urinary particle analyzer 3, and a collection unit 56 for collecting the specimen rack 7a that has gone through the measurement by the urinary particle analyzer 3.

Figure 8:
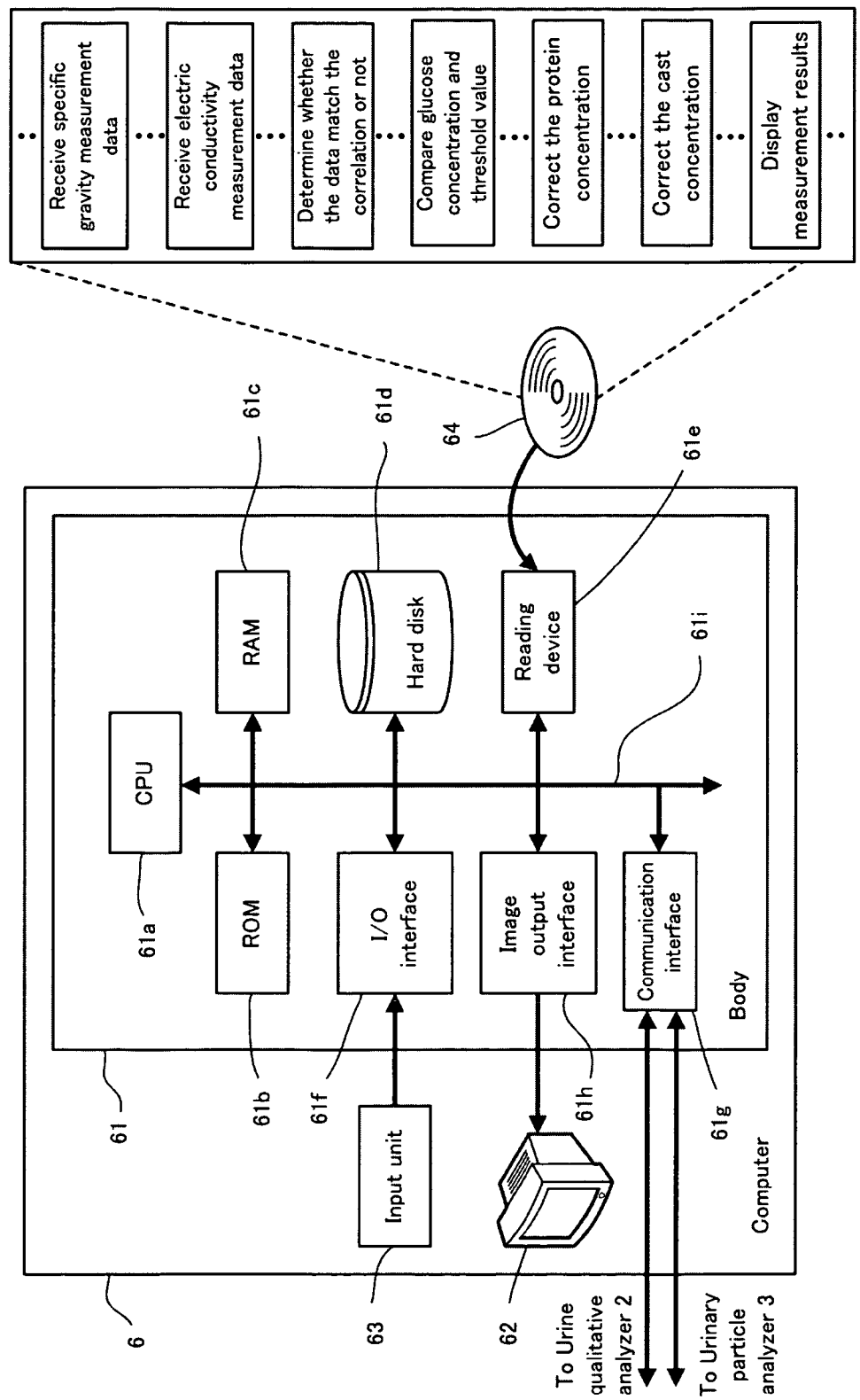
FIG. 8 is a block diagram showing a construction of a computer that the urine analysis system according to an embodiment of the present invention has.

Next, a construction of the computer 6 will be described. FIG. 8 is a block diagram showing a construction of the computer 6 that the urine analysis system according to an embodiment of the present invention has. The computer 6 is mainly constructed with a main body 61, an image display unit 62, and an input unit 63. The main body 61 is mainly constructed with a CPU 61a, a ROM 61b, a RAM 61c, a hard disk 61d, a reading device 61e, an input/output interface 61f, a communication interface 61g, and an image output interface 61h. The CPU 61a, the ROM 61b, the RAM 61c, the hard disk 61d, the reading device 61e, the input/output interface 61f, the communication interface 61g, and the image output interface 61h are connected via a bus 61i.

The CPU 61a can execute computer programs stored in the ROM 61b and computer programs loaded in the RAM 61c. The CPU 61a executes computer programs such as described later, whereby the computer 6 functions as a measurement result correction apparatus according to the present invention.

The ROM 61b is constructed with a mask ROM, a PROM, an EPROM, an EEPROM, or the like, and records the computer programs executed by the CPU 61a and the data used therefor.

The RAM 61c is constructed with an SRAM, a DRAM, or the like. The RAM 61c is used for reading the computer programs recorded in the ROM 61b and the hard disk 61d. Also, the RAM 61c is used as a work area of the CPU 61a when these computer programs are executed.

Various computer programs to be executed by the CPU 61a, such as an operating system and application programs, as well as data used for execution of the computer programs are installed in the hard disk 61d.

The reading device 61e is constructed with a flexible disk drive, a CD-ROM drive, a DVD-ROM drive, or the like, and can read the computer programs or data recorded in the transportable recording medium 64. Also, the transportable recording medium 64 stores a computer program that functions as the measurement result correction apparatus according to the present invention. The computer 6 can read the computer program according to the present invention from the transportable recording medium 64, and can install the computer program into the hard disk 61d.

Here, the aforesaid computer program can be supplied not only by the transportable recording medium 64 but also from an outside apparatus which is communicably connected to the computer 6 with an electric communication line (irrespective of whether it is wired or wireless), via the electric communication line. For example, the computer program can be stored in a hard disk of a server computer on the Internet, and the computer 6 can make access to the server computer to download the computer program and install this into the hard disk 61d.

Also, an operating system that supplies a graphical user interface environment such as the Windows (registered trademark) manufactured and sold by the Microsoft Corporation in the United Conditions is installed in the hard disk 61d. In the following description, the computer program according to the present embodiment is assumed to operate on the aforesaid operating system.

Figure 9:
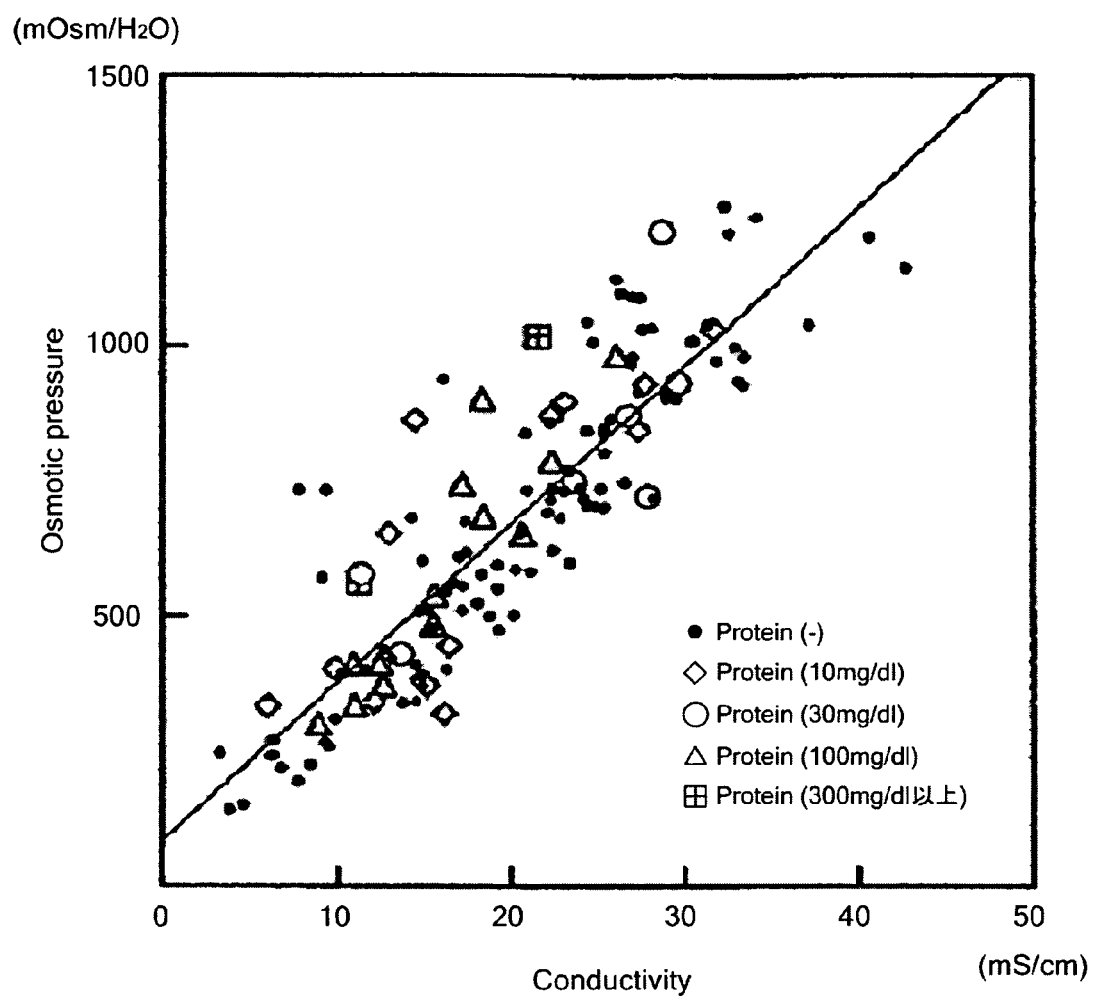
FIG. 9 is a graph showing a result of an experiment in which the influence of protein concentration in urine on electric conductivity has been surveyed.
Figure 10:
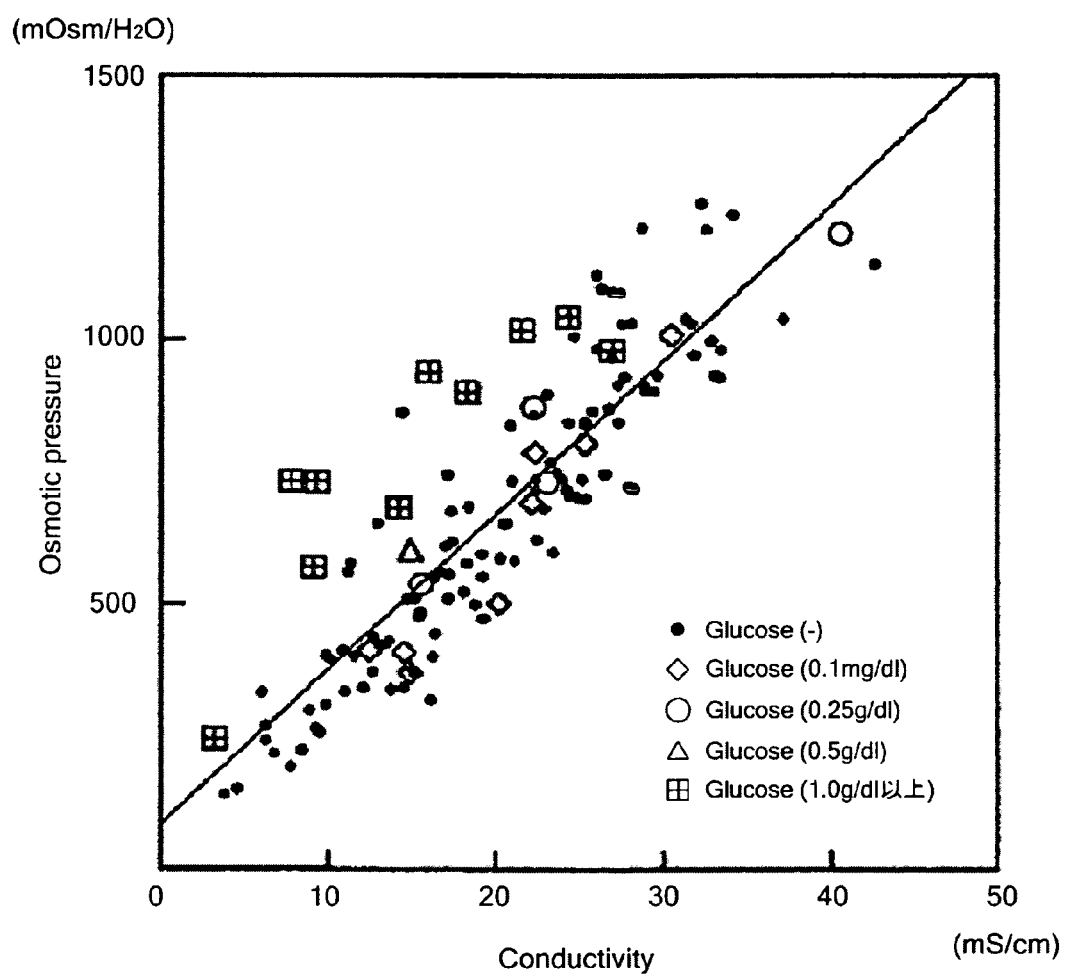
FIG. 10 is a graph showing a result of an experiment in which the influence of glucose concentration in urine on electric conductivity has been surveyed.

Also, the hard disk 61d stores a threshold value related to results of measurement of glucose concentration, which is used for determining whether the electric conductivity measured by the urinary particle analyzer 3 has a low reliability or not. The inventors of the present invention have conducted an experiment to examine the influence given to the electric conductivity by the sugar concentration and the protein concentration in urine. FIG. 9 is a graph showing a result of an experiment on the protein concentration, and FIG. 10 is a graph showing a result of an experiment on the glucose concentration. In FIGS. 9 and 10, the vertical axis represents the osmotic pressure (mOsm/$H_2$O), and the horizontal axis represents the electric conductivity (mS/cm). Specific gravity and Osmotic pressure are known to be highly correlated, and are assumed to have substantially the same clinical significance. Therefore, in the present embodiment, an experiment has been carried out on the relationship between the electric conductivity and the osmotic pressure instead of carrying out an experiment on the relationship between the electric conductivity and the specific gravity. In FIG. 9, the results of measurement on the electric conductivity and the osmotic pressure when no protein has been detected in the specimens are shown by dots; the results of measurement when protein of about 15 mg/dl has been detected in the specimens are shown by rhombuses; the results of measurement when protein of about 30 mg/dl has been detected in the specimens are shown by circles; the results of measurement when protein of about 100 mg/dl has been detected in the specimens are shown by triangles; and the results of measurement when protein of 300 mg/dl or more has been detected in the specimens are shown by squares. As shown in FIG. 9, the measurement results of the specimens in which protein of 300 mg/dl or more has been detected are greatly deviated from the line indicating the correlation between the osmotic pressure and the electric conductivity, thereby showing that those measurement results have a low reliability. Also, this experiment result shows that the measurement results of the specimens in which protein of about 15 mg/dl has been detected, the specimens in which protein of about 30 mg/dl has been detected, and the specimens in which protein of about 100 mg/dl has been detected are greatly deviated from the line indicating the correlation.

In FIG. 10, the results of measurement on the electric conductivity and the osmotic pressure when no glucose has been detected in the specimens are shown by dots; the results of measurement when glucose of about 0.1 g/dl has been detected in the specimens are shown by rhombuses; the results of measurement when glucose of about 0.25 g/dl has been detected in the specimens are shown by circles; the results of measurement when glucose of about 0.5 g/dl has been detected in the specimens are shown by triangles; and the results of measurement when glucose of 1.0 g/dl or more has been detected in the specimens are shown by squares. As shown in FIG. 10, the measurement results of the specimens in which glucose of 1.0 g/dl or more has been detected are greatly deviated from the line indicating the correlation between the osmotic pressure and the electric conductivity, thereby showing that those measurement results have a low reliability. Also, this experiment result shows that the measurement results of the specimens having a high glucose concentration are greatly deviated from the line indicating the correlation more conspicuously than the experiment results on protein. Also, it will be understood that the measurement results of the specimens other than the specimens in which glucose of 1.0 g/dl or more has been detected are not greatly deviated from the line indicating the correlation.

Figure 11:
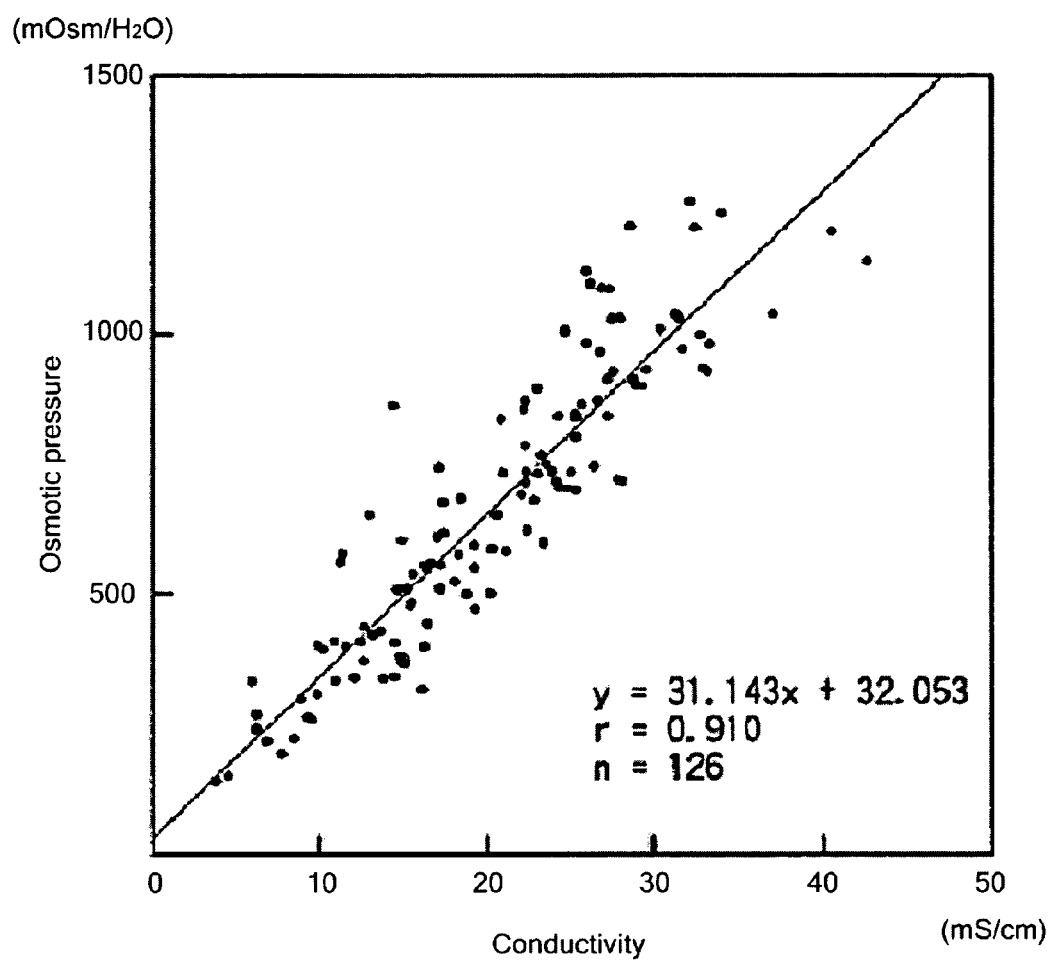
FIG. 11 is a graph in which the result of measurement of specimens having a high glucose concentration has been removed from the graph of correlation between the electric conductivity and the osmotic pressure shown in FIG. 10.

FIG. 11 shows a graph in which the result of measurement of specimens having a high glucose concentration has been removed from the graph of correlation between the electric conductivity and the osmotic pressure shown in FIG. 10. As shown in FIG. 11, the graph clearly has a higher correlation than the correlation shown in FIGS. 9 and 10. The correlation coefficient in the experiment result of FIG. 11 is 0.91, showing an improvement as compared with the experiment result in FIGS. 9 and 10 in which the correlation coefficient is 0.869. These results seem to be due to the fact that protein and sugar are not electrolytes, and therefore, a higher concentration of these decreases the electric conductivity as a non-conductor.

In this way, the inventors of the present invention have found out that the results of measurement of the electric conductivity on the specimens having a high protein concentration and sugar (including glucose) concentration are deviated from the correlation with the osmotic pressure (specific gravity) of urine acting as an important index on the malfunction of the kidney, and hence have a low reliability as clinical data. Therefore, in this embodiment, the threshold value related to the result of measurement of the glucose concentration, which is used for determining whether the electric conductivity measured by the urinary particle analyzer 3 has a low reliability or not, is set to be 1.0 g/dl.

The input/output interface 61f is constructed, for example, with a serial interface such as USB, IEEE1394, or RS-232C, a parallel interface such as SCSI, IDE, or IEEE1284, an analog interface made of a D/A converter, an A/D converter, or the like, and others. An input unit 63 made of a keyboard and a mouse is connected to the input/output interface 61f, whereby the user can input data into the computer 6 by using the input unit 63.

The communication interface 61g is, for example, an Ethernet (registered trademark) interface, whereby the computer 6 can transmit and received data to and from the urine qualitative analyzer 2, the urinary particle analyzer 3, and the conveyance device 4, 5 via the communication interface 61g by using a predetermined communication protocol.

The image output interface 61h is connected to the image display unit 62 constructed with an LCD, a CRT, or the like, and is adapted to output an image signal to the image display unit 62 in accordance with the image data given from the CPU 61a. The image display unit 62 displays an image (screen) in accordance with the input image signal.

Next, operation of the urine analysis system 1 according to this embodiment will be described. First, a specimen rack 7a that houses a plurality of specimen containers 7, in which a specimen (urine) is housed, is automatically transported to a measurement position at the front of the urine qualitative analyzer 2. Specifically, the specimen rack 7a that houses a plurality of specimen containers 7, in which a specimen is housed, is first set at the sending unit 44 of the conveyance device 4. Then, the user presses the start key disposed on the input panel 42. By this, the conveyance device 4 starts to operate, whereby the specimen rack 7a set in the sending unit 44 of the conveyance device 4 is transported to the lateral conveyor 45. Then, in the lateral conveyor 45, the specimen rack 7a is successively sent laterally at a pitch corresponding to one specimen container 7, whereby the specimen containers 7 housed in the specimen rack 7a are transported to the measurement position of the urine qualitative analyzer 2. Then, in the first measuring unit 23 and the second measuring unit 24 of the urine qualitative analyzer 2, the specimen contained in the specimen container 7 housed in the specimen rack 7a is successively measured. Thereafter, the specimen rack 7a is transported from the lateral conveyor 45 to the discharge unit 46, and is transported to the sending unit 54 of the conveyance device 5. Then, the conveyance device 5 starts to operate by detecting with a sensor disposed in the sending unit 54 that the specimen rack 7a has been transported to the sending unit 54.

The specimen rack 7a transported to the sending unit 54 of the conveyance device 5 is transported to the lateral conveyor 55 of the conveyance device 5. Then, in the lateral conveyor 55, the specimen rack 7a is successively sent laterally at a pitch corresponding to one specimen container 7, whereby the specimen containers 7 housed in the specimen rack 7a are transported to the measurement position of the urinary particle analyzer 3. Then, in the measuring unit 33 of the urinary particle analyzer 3, the specimen contained in the specimen container 7 housed in the specimen rack 7a is successively measured. Thereafter, the specimen rack 7a is transported from the lateral conveyor 55 to the collection unit 56. The operation such as described above is successively carried out for each specimen rack 7a.

Figure 12:
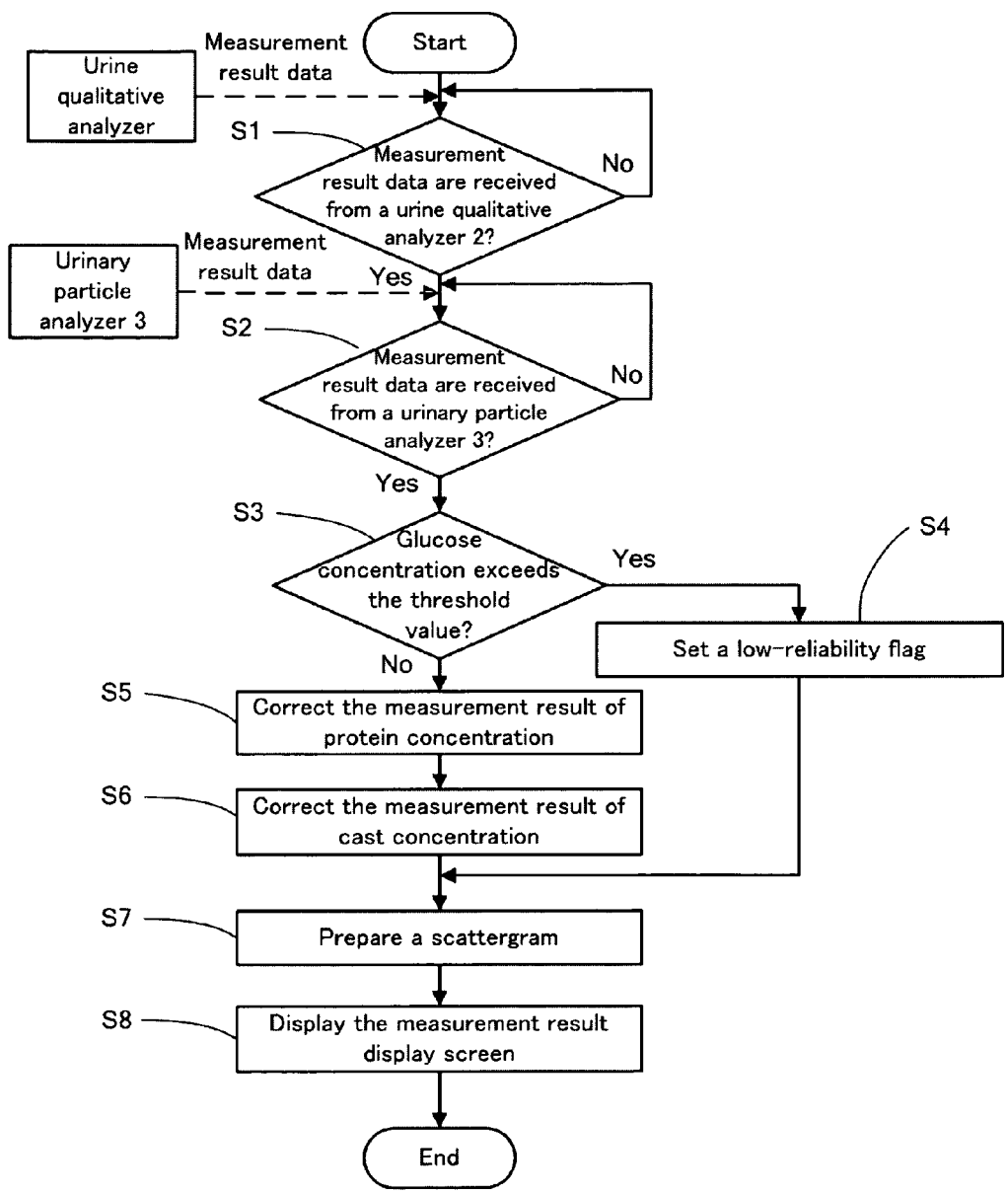
FIG. 12 is a flowchart showing a procedure of a process for correction of a measurement result according to an embodiment of the present invention.

In this manner, the measurement result data that the urine qualitative analyzer 2 and the urinary particle analyzer 3 have obtained by measuring the same specimen are transmitted to the computer 6. Then, the computer 6 performs a correction process on the measurement results. Hereafter, the measurement result correction process of the computer 6 will be described. FIG. 12 is a flowchart showing a procedure of a process for correction of a measurement result by a computer program that the computer 6 executes according to an embodiment of the present invention. Here, with regard to the low reliability flag described later, the cleared condition is assumed to be a default value. First, the CPU 61a of the computer 6 waits for receipt of the measurement result data from the urine qualitative analyzer 2 (step S1). When the measurement result data have been received (Yes in the step S1), the CPU 61a waits for receipt of the measurement result data from the urinary particle analyzer 3 (step S2). Then, when the measurement result data have been received in the step S2 (Yes in the step S2), the CPU 61a compares the measurement result of glucose concentration with the threshold value that is used in determining whether the electric conductivity measured by the urinary particle analyzer 3 has a low reliability or not (step S3). In the step S3, when the measurement result of glucose concentration exceeds the threshold value (Yes in the step S3), the CPU 61a sets the low reliability flag on the measurement result of the electric conductivity (step S4).

In contrast, in the step S3, when the measurement result of glucose concentration does not exceed the threshold value (No in the step S3), the CPU 61a corrects the measurement result of protein concentration in accordance with the following formula (1) (step S5).

Corrected protein concentration=measured value of protein concentration×standard electric conductivity/electric conductivity     (1)

Here, the standard electric conductivity is assumed to be 25 mS/cm. The reason therefor will be described below. When there is decrease in the plasma osmotic pressure (polydipsia), the secretion of ADH (antidiuretic hormone) will decrease to restrain the reabsorption of water in the kidney, so that a large amount of water is excreted in the urine, thereby leading to decrease in the osmotic pressure of the urine. Also, the osmotic pressure of the urine is nearly inversely proportional to the concentration of electrolytes such as creatinine, Na, K, Cl, and the like contained in the urine, and therefore the electric conductivity of the urine that varies in accordance with the concentration of the electrolytes in the urine is highly correlated to the urine osmotic pressure. In this manner, the electric conductivity of the urine reflects the degree of concentration/dilution of the urine. Therefore, by normalizing the protein concentration with the electric conductivity of the urine as in the above formula (1), the effect of concentration/dilution of the urine can be removed from the protein concentration to obtain a highly reliable protein concentration. Also, in the Fishberg concentration test for examining the concentration function of the kidney, the urine concentration function can be assumed to be normal if the urine specific gravity is 1.025 or higher or the osmotic pressure is 850 mOsm/kg.$H_2O$ at least once in urine tests carried out for three-times. For this reason, in the present embodiment, the value of 25 mS/cm which is a value corresponding to the urine specific gravity of 1.025 and the osmotic pressure of 850 mOsm/kg.$H_2O$ is adopted as the standard electric conductivity constituting the reference value for making corrections.

Next, the CPU 61a corrects the measurement result of cast concentration in accordance with the following formula (2) (step S6).

Corrected cast concentration=measured value of cast concentration×standard electric conductivity/electric conductivity     (2)

Here, the standard electric conductivity is assumed to be 25 mS/cm in the same manner as in the formula (1). The reason therefor is the same as described above.

Then, the CPU 61a prepares scattergrams based on the measurement results of the urinary particle analyzer 3 (step S7), displays a measurement result display screen on the image display unit 62 (step S8), and ends the process.

Figure 13:
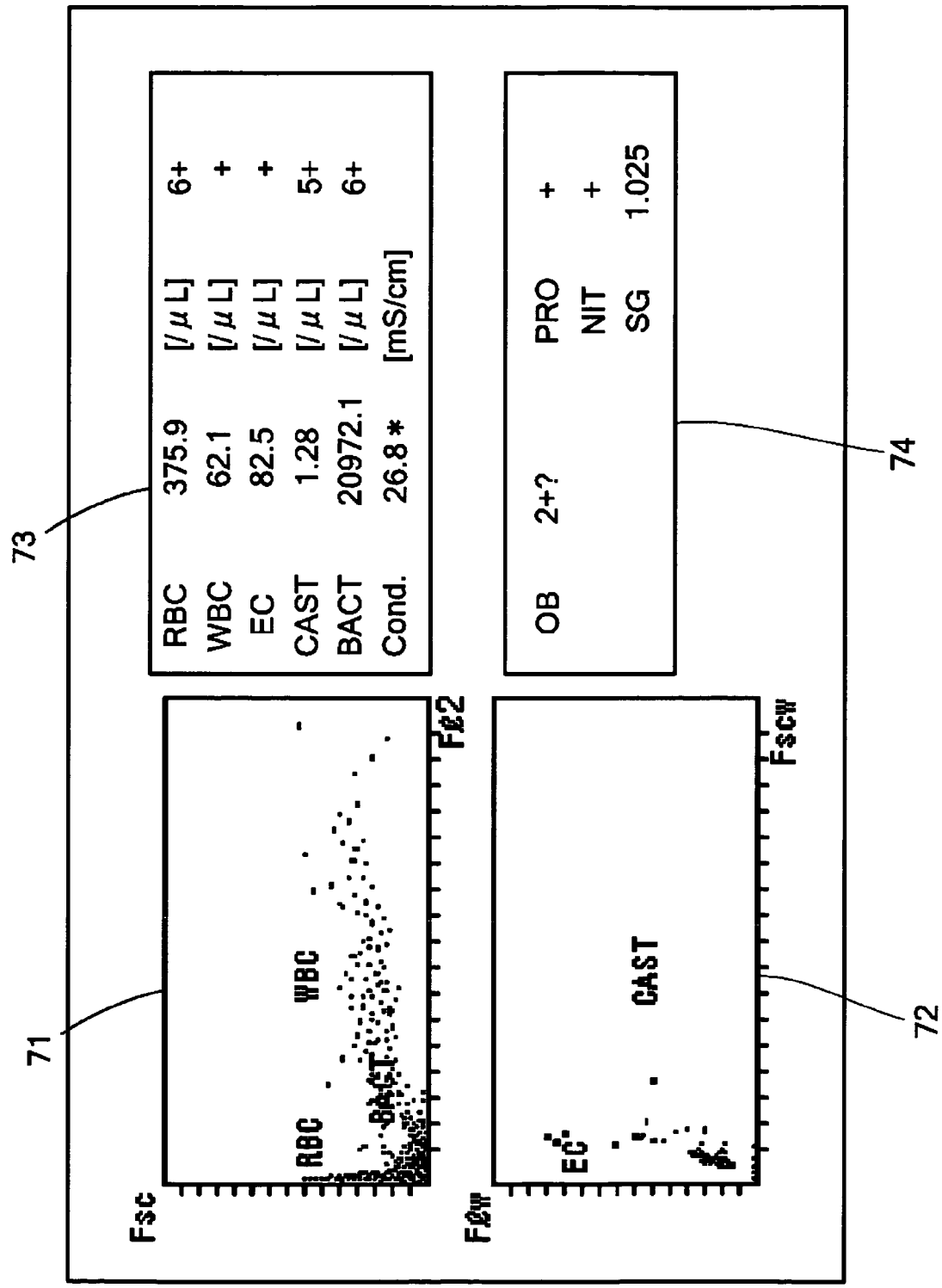
FIG. 13 is a model view illustrating one example of a measurement result display screen that the computer according to an embodiment of the present invention displays on an image display unit.

FIG. 13 is a model view illustrating one example of a measurement result display screen that the computer 6 according to this embodiment displays on the image display unit 62. Referring to FIG. 13, scattergrams and the measured value of each measurement item are displayed on the measurement result display screen. To describe it further in detail, two scattergrams 71, 72 prepared on the basis of the scattered light information and fluorescence information are displayed by being vertically arranged from the center to the left of the measurement result display screen, and measured value display areas 73, 74 are displayed by being vertically arranged from the center to the right of the measurement result display screen. In the measured value display area 73 on the upper side, the measured values of red blood cell concentration (RBC), white blood cell concentration (WBC), epithelial cell concentration (EC), cast concentration (CAST), bacteria concentration (BACT), and electric conductivity (Cond.) among the measurement results of the urinary particle analyzer 3 are displayed. Further, in the measured value display area 74 on the lower side, the measured values of occult blood concentration (OB), protein concentration (PRO), nitrite concentration (NIT), and specific gravity (SG) among the measurement results of the urine qualitative analyzer 2 are displayed. When the low-reliability flag is set in the measurement result of the electric conductivity, a symbol "*" stating that the data have a low reliability is displayed on the lateral side of the measurement value. FIG. 13 shows a screen in which the symbol "*" is displayed on the lateral side of the measured value of the electric conductivity. By doing so, the user can be informed that the measured value of the electric conductivity has a low reliability.

Also, in such a measurement result display screen, when the low-reliability flag is cleared, the corrected measurement results of protein concentration and cast concentration are displayed. When the low-reliability flag is set, the correction operation is not carried out, as described above, so that the measurement results of protein concentration and cast concentration are displayed without correction. This is due to the following reason. Since the measurement result of electric conductivity cannot be relied upon, the corrected values scarcely have reliability even if the protein concentration and the cast concentration are corrected using the electric conductivity such as described above.

The inventors of the present invention have conducted an experiment to compare the corrected measurement results of cast concentration with the measurement results of cast concentration without correction. In this experiment, the number of specimens is 228, and the standard for determining that the cast concentration is significant, i.e. that the kidney function is abnormal by cast concentration, is such that the cast concentration is 2.5 casts/µl or higher or the concentration of casts containing substances (red blood cells or white blood cells) is 1.0 casts/µl or higher. FIG. 14 is a view table showing a result of this experiment. Referring to FIG. 14, the number of specimens determined to have a protein concentration of +2, +3 is 52, and the number of specimens determined to have a protein concentration of +1 is 22. Similarly, the number of specimens determined to have a protein concentration of ± is 10, and the number of specimens determined to have a protein concentration of 0 is 144. With the cast concentration before correction, twelve specimens are determined to be significant when the protein concentration is +2, +3; two specimens are determined to be significant when the protein concentration is +1; one specimen is determined to be significant when the protein concentration is ±; and five specimens are determined to be significant when the protein concentration is 0.

In contrast, with the corrected cast concentration, seventeen specimens are determined to be significant when the protein concentration is +2, +3; four specimens are determined to be significant when the protein concentration is +1; two specimens are determined to be significant when the protein concentration is ±; and six specimens are determined to be significant when the protein concentration is 0. In this manner, with the corrected cast concentration, the number of specimens determined to be significant is larger in each case. This seems to be due to the fact that the abnormal specimens that could not be detected by the cast concentration before correction due to varied urine concentration can be detected by the corrected cast concentration from which the influence of the urine concentration has been removed. In this manner, it will be understood that, with the measurement result correction method according to this embodiment, the function of the kidney can be evaluated more accurately than in the prior art.

With the construction such as described above, in the urine analysis system 1 according to an embodiment of the present invention, the concentrations of protein and casts, which are components related to the condition of the kidney, are respectively corrected with the use of the electric conductivity that reflects the degree of concentration/dilution of urine nearly accurately, so that the influence of concentration/dilution of urine can be removed from these concentrations, thereby obtaining a highly reliable measurement result. Also, as compared with the conventional correction method that uses creatinine concentration, correction having an extremely high precision and a high reliability can be made by using the electric conductivity having a much higher resolution than in the measurement of creatinine concentration by the colorimetry.

Here, in the urine analysis system 1 according to the above-described embodiment, a construction has been described in which the urine qualitative analyzer 2 measures the specific gravity by the refractive index of the specimen; however the construction is not limited to this alone, so that a construction of measuring the specific gravity by a test paper may be adopted, for example. However, it is preferable to adopt a construction of measuring the specific gravity by the refractive index because the measurement of specific gravity by the refractive index has a higher resolution and hence can expect to have a higher measurement precision than the measurement of specific gravity by using a test paper.

Also, in the urine analysis system 1 according to this embodiment, a construction has been described in which the reliability of the measurement result of electric conductivity is evaluated by using the glucose concentration; however, the construction is not limited to this alone, so that a construction of evaluating the measurement result of electric conductivity by using the concentration of a sugar other than glucose may be adopted, or alternatively a construction of evaluating the measurement result of electric conductivity by using the protein concentration may be adopted. Further, a construction may be adopted in which the protein concentration and the cast concentration are corrected uniformly by the electric conductivity without evaluating the measurement result of electric conductivity or regardless of the evaluation of the measurement result of electric conductivity.

Also, in the urine analysis system 1 according to this embodiment, a construction has been described in which the urine qualitative analyzer 2 and the urinary particle analyzer 3 are connected to the computer 6, whereby the measurement results of the urine qualitative analyzer 2 and the urinary particle analyzer 3 are transmitted to the computer 6, so as to make the computer 6 correct the protein concentration and the cast concentration; however, the construction is not limited to this alone, so that a function as a measurement result correction apparatus, for example, can be mounted on the urinary particle analyzer 3. In this case, the urine qualitative analyzer 2 and the urinary particle analyzer 3 are connected with each other, whereby the measurement results of the urine qualitative analyzer 2 are transmitted to the urinary particle analyzer 3, so as to make the urinary particle analyzer 3 correct the measurement results of cast concentration obtained by the urinary particle analyzer 3 and the measurement results of protein concentration received from the urine qualitative analyzer 2. Also, the display screen displayed on the image display unit 62 of the computer 6 such as described above may be displayed on a display unit such as an LCD disposed in the urinary particle analyzer 3. Also, it is still more preferable to adopt a construction in which an input device of touch panel type is attached to this display unit, whereby an input is made with the fingers of the user or a stylus instead of an input by a mouse. Further, the urine qualitative analyzer 2 and the urinary particle analyzer 3 may be integrated, and a function as a measurement result correction apparatus may be mounted on this integrated analyzer. In this case, measurement is made within one apparatus on the measurement items of the urine qualitative analyzer 2 and the measurement items of the urinary particle analyzer 3 and, among the measurement results of these, the protein concentration and the cast concentration are corrected on the basis of the electric conductivity. In this case also, the display screen such as described above may be displayed on a display unit such as an LCD disposed in the apparatus, and it is still more preferable to adopt a construction in which an input device of touch panel type is attached to this display unit, whereby an input is made with the fingers of the user or a stylus.

Also, in the urine analysis system 1 according to this embodiment, a construction has been described in which the low-reliability flag is displayed with a symbol "*"; however, the construction is not limited to this, so that the low-reliability flag may be displayed with the letters "low reliability" or a construction can be adopted in which the low-reliability flag is displayed by another display method such as one in which the measured values to which the low-reliability flag is set are displayed in blue.

Also, in the urine analysis system 1 according to this embodiment, a construction has been described in which the measurement of electric conductivity is made on samples controlled to have a constant temperature; however, the construction is not limited to this alone, so that a construction may be adopted in which, for example, the measurement results of electric conductivity are subjected to temperature correction. However, since it is difficult to obtain a correct electric conductivity by temperature correction, it is preferable to adopt a construction in which the samples are controlled to have a constant temperature in view of obtaining highly precise measurement results of electric conductivity.

Also, in this embodiment, a construction has been described in which the standard electric conductivity is set to be 25 mS/cm; however, the construction is not limited to this alone, so that any value can be adopted as the standard electric conductivity. However, the urine electric conductivity that can be expected when the concentration function of the kidney is normally operating is from 18 to 25 mS/cm, so that, by setting the standard electric conductivity to be within this range, the protein concentration and the cast concentration can be converted into those at the electric conductivity of normal urine. Therefore, it is preferable to set the standard electric conductivity to be within this range because of the convenience in evaluating the measurement results, such as comparison with other measurement results of protein concentration and cast concentration that have not been corrected.

Also, in this embodiment, a construction has been described in which the protein concentration and the cast concentration are objects of correction. Casts are made of protein that is solidified like a gelatin in the kidney, and the cast concentration is known to reflect the reabsorption capability of the kidney. Also, this cast concentration changes in accordance with the degree of concentration of the urine in a manner similar to the protein concentration. Therefore, by treating the cast concentration as an object of correction, a cast concentration that correctly reflects the function of the kidney can be obtained. However, it is not limited to such a construction, so that a construction may be adopted in which an in-urine component related to the condition of the kidney, particularly the in-urine component that reflects the reabsorption capability of the kidney such as glucose, for example, is treated as an object of correction. Also, a construction may be adopted in which only one of the protein concentration and the cast concentration is treated as an object of correction. However, by correcting the protein concentration, a protein concentration from which the influence of the degree of concentration of the urine is removed can be obtained, thereby the kidney function can be evaluated using protein concentration at a higher precision than in the prior art. Also, by correcting the cast concentration, a cast concentration from which the influence of the degree of concentration of the urine is removed can be obtained, whereby the kidney function can be evaluated using cast concentration at a higher precision than in the prior art. In addition, a specimen with an abnormal kidney function that cannot be detected only by one measurement result, such as a case in which the cast concentration is abnormal though the protein concentration is normal, can be detected. Therefore, it is preferable to adopt a construction in which both the protein concentration and the cast concentration are corrected.

Also, the current urine protein test paper may sometimes react with a protein species other than those of glomerulus origin, such as tissue protein, though the test paper reacts with albumin in a sensitive manner. Also, according to the reaction principle, an alkaline urine or a highly buffered urine may exhibit pseudo-positiveness. For this reason, the measurement result of protein concentration itself may lack in reliability. In this case, even if the protein concentration is corrected with the creatinine concentration, the corrected protein concentration also is insufficiently reliable. In contrast to this, the cast concentration raises a reliability problem to a less degree than the protein concentration. Therefore, by treating the cast concentration as an object of correction and correcting this cast concentration with the electric conductivity, a highly reliable measurement result of cast concentration can be obtained. By using this measurement result for evaluation of the kidney function, the precision of kidney function evaluation can be improved as compared with the prior art.

Also, in this embodiment, a construction has been described in which the cast concentration is measured, and this is corrected with the use of the electric conductivity; however, the construction is not limited to this alone, so that a construction may be adopted in which the concentration of casts containing red blood cells or white blood cells is measured, and this cast concentration is corrected with the use of the electric conductivity. By doing so, it is possible to obtain in a highly precise manner the concentration of casts containing red blood cells or white blood cells that can distinguish the condition (pathology) of the kidney in further detail, so that the evaluation of the kidney condition can be made further more correctly.

Also, in this embodiment, a construction has been described in which the urinary particle analyzer 3 measures an impedance change within a sample that flows through the orifice 33e of the sheath flow cell 33c and the scattered light and the fluorescence when a laser beam is emitted to the sample, so as to detect the morphology of the particles contained in the sample; however, the construction is not limited to this alone, so that a construction may be adopted in which images of a particle passing through the orifice 33e are captured with a video camera, and the obtained captured images are analyzed by an image processing so as to detect the morphology of this particle.

The foregoing detailed description and accompanying drawings have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

What is claimed is:

1. A measurement result correction method comprising the steps of:
   measuring a value of a concentration of a component in urine, the component being related to a kidney condition;
   measuring an electric conductivity of said urine;
   correcting the measured value of the concentration of the component on a basis of the measured electric conductivity of the urine;
   outputting the corrected value of the concentration of the component;
   wherein the step of correcting is performed to correct the measured value of the concentration of the component on the basis of the measured electric conductivity of the urine when reliability of the measured electric conductivity is high, and is performed so as not to correct the measured value of the concentration of the component on the basis of the measured electric conductivity of the urine when reliability of the measured electric conductivity is low; and
   the step of outputting is performed so as to output the corrected value of the concentration of the component when reliability of the measured electric conductivity is high, and is performed so as not to output the non-corrected measured value of the concentration of the component when reliability of the measured electric conductivity is low.

2. The measurement result correction method of claim 1, wherein the component is casts or protein.

3. The measurement result correction method of claim 1, further comprising the steps of:
   measuring a value of a concentration of a glucose or a protein in said urine; and
   determining that reliability of the measured electric conductivity is high when the measured value of the concentration of the glucose or the protein does not exceed a predetermined threshold value, and determining that reliability of the measured electric conductivity is low when the measured value of the concentration of the glucose or the protein exceeds the predetermined threshold value,
   wherein the step of correcting is performed so as to correct the measured value of the concentration of the component on the basis of the measured electric conductivity of the urine when determined that reliability of the measured electric conductivity is high, and is performed so as not to correct the measured value of the concentration of the component on the basis of the measured electric conductivity of the urine when determined that reliability of the measured electric conductivity is low; and
   the step of outputting is performed so as to output the corrected value of the concentration of the component when determined that reliability of the measured electric conductivity is high, and is performed so as to output the non-corrected measured value of the concentration of the component when determined that reliability of the measured electric conductivity is low.

4. A measurement result correction system comprising:
- a first measuring unit being configured to measure a value of a concentration of a component in urine, the component being related to a kidney condition;
- a second measuring unit being configured to measure an electric conductivity of said urine;
- a computer being programmed to receive the measured value of the concentration of the component from the first measuring unit, receive the measured electric conductivity of the urine from the second measuring unit, and correct the measured value of the concentration of the component on a basis of the measured electric conductivity of the urine;
- an output section being configured to output the corrected value of the concentration of the component obtained by said computer;
- wherein the computer is programmed to correct the measured value of the concentration of the component on the basis of the measured electric conductivity of the urine when reliability of the measured electric conductivity is high, and not to correct the measured value of the concentration of the component on the basis of the measured electric conductivity of the urine when reliability of the measured electric conductivity is low; and
- the output section is configured to output the corrected value of the concentration of the component obtained by the computer when reliability of the measured electric conductivity is high, and to output the non-corrected measured value of the concentration of the component obtained by said first measuring unit when reliability of the measured electric conductivity is low.

5. The measurement result correction system of claim 4, wherein said computer is programmed to multiply the measured value of the concentration of the component by a factor that is obtained by dividing a predetermined standard electric conductivity with the measured electric conductivity of the urine in order to correct the measured value of the concentration of the component.

6. The measurement result correction system of claim 5, wherein said standard electric conductivity is an electric conductivity from 18 mS/cm to 25 mS/cm.

7. The measurement result correction system of claim 4, wherein the component is casts.

8. The measurement result correction system of claim 4, wherein said first measuring unit comprises:
- a flow cell provided with an orifice through which a sample containing the urine is let to pass;
- a light-emitting element that emits light to said orifice; and
- a light-receiving element that receives light emitted from said orifice; and
- a processing section being configured to determine a morphology of a urinary particle that passes through said orifice on a basis of light received by said light-receiving element.

9. The measurement result correction system of claim 7, further comprising:
- a first analyzer being configured to measure a value of a protein concentration of said urine; and
- a second analyzer that includes said first measuring unit and said second measuring unit,
- wherein said computer is programming to
  - receive the measured value of the protein concentration of said urine from the first analyzer; and
  - correct the measured value of the protein concentration on a basis of said electric conductivity of the urine measured by said second measuring unit.

10. The measurement result correction system of claim 4, further comprising:
- a urine qualitative analyzer having said first measuring unit, wherein the component is protein.

11. The measurement result correction system of claim 4, further comprising:
- a temperature control unit being configured to control a temperature of the urine.

12. The measurement result correction system of claim 4, further comprising:
- a glucose concentration measuring unit being configured to measure a value of a glucose concentration of the urine; and
- a comparison section for comparing the measured value of the glucose concentration with a predetermined threshold value, and
- wherein said output section is configured to output information indicating that reliability of the measured electric conductivity is low when a comparison result of the comparison section indicates the measured value of the glucose concentration exceeds the threshold value.

13. The measurement result correction system of claim 4, further comprising:
- a glucose concentration measuring unit being configured to measure a value of a glucose concentration of the urine; and
- a comparison section for comparing the measured value of the glucose concentration with a predetermined threshold value,
- wherein said computer is programmed not to correct the measured value of the concentration of the component when a comparison result of the comparison section indicates the measured value of the glucose concentration exceeds the threshold value.

14. A urine analyzer comprising:
- a first measuring unit being configured to measure a value of a concentration of a component in urine, the component being related to a kidney condition;
- a second measuring unit being configured to measure an electric conductivity of the urine;
- a controller being programmed to perform predetermined operations comprising receiving the measured value of the concentration of the component from the first measuring unit, receiving the measured electric conductivity of the urine from the second measuring unit, and correcting the measured value of the concentration of the component on a basis of the measured electric conductivity of the urine;
- an output section being configured to output the corrected value of the concentration of the component obtained by said controller;
- wherein the controller is programmed to correct the measured value of the concentration of the component on the basis of the measured electric conductivity of the urine when reliability of the measured electric conductivity is high, and not to correct the measured value of the concentration of the component on the basis of the measured electric conductivity of the urine when reliability of the measured electric conductivity is low; and
- the output section is configured to output the corrected value of the concentration of the component obtained by the controller when reliability of the measured electric conductivity is high, and to output the non-corrected measured value of the concentration of the component obtained by said first measuring unit when reliability of the measured electric conductivity is low.

15. The urine analyzer of claim 14, further comprising:

a protein concentration obtaining unit being configured to obtain a value of a protein concentration of said urine, and wherein said controller is programmed to correct the value of the protein concentration obtained by said protein concentration obtaining unit on a basis of said measured electric conductivity of the urine.

16. The urine analyzer of claim 15, wherein said protein concentration obtaining unit is configured to obtain the value of the protein concentration from an apparatus other than the urine analyzer.

\* \* \* \* \*